US012685527B2

(12) United States Patent
Young et al.

(10) Patent No.: US 12,685,527 B2
(45) Date of Patent: Jul. 21, 2026

(54) SURGICAL INSTRUMENT FOR MANIPULATING AND PASSING SUTURE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Timothy Young, Upton, MA (US); Marc J. Balboa, Hopkinton, MA (US); Kangqiao Li, Providence, RI (US); Justin A. Barbas, West Bridgewater, MA (US); Alyssa Paul, Mansfield, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 433 days.

(21) Appl. No.: 18/032,021

(22) PCT Filed: Oct. 28, 2021

(86) PCT No.: PCT/US2021/057032
§ 371 (c)(1),
(2) Date: Apr. 14, 2023

(87) PCT Pub. No.: WO2022/094065
PCT Pub. Date: May 5, 2022

(65) Prior Publication Data
US 2024/0016490 A1　　Jan. 18, 2024

Related U.S. Application Data

(60) Provisional application No. 63/219,671, filed on Jul. 8, 2021, provisional application No. 63/106,713, filed on Oct. 28, 2020.

(51) Int. Cl.
*A61B 17/04* (2006.01)

(52) U.S. Cl.
CPC .................................. *A61B 17/0485* (2013.01)

(58) Field of Classification Search
CPC . A61B 17/0483; A61B 17/0485; A61B 17/06; A61B 17/06066; A61B 17/06109; A61B 2017/061; A61B 2017/06142
See application file for complete search history.

(56) References Cited

U.S. PATENT DOCUMENTS 4,816,018 A * 3/1989 Parisi .................. A61F 9/00745
606/128
9,198,655 B2 12/2015 Skinlo et al.
(Continued)

*Primary Examiner* — Diane D Yabut
*Assistant Examiner* — Christian D Knauss
(74) *Attorney, Agent, or Firm* — Kate Ryland Tetzlaff

(57) ABSTRACT

An instrument for manipulating and passing suture through a tissue is disclosed. The instrument includes a handle and a needle. The needle includes a lumen and terminates with a distal opening and a sharp edge surface for piercing tissue. The instrument also includes a hook, axially slideable within the needle lumen and through the needle distal opening. The hook may axially slide between a suture-locking configuration, a suture-sliding configuration and a suture release and capture configuration. The instrument may include improvements that better protect smaller and more fragile sutures.

18 Claims, 14 Drawing Sheets

(56)  References Cited

U.S. PATENT DOCUMENTS

| | | | |
|---|---|---|---|
| 10,667,805 B1 | 6/2020 | Bourland, III et al. | |
| 10,765,420 B2 | 9/2020 | Lunn et al. | |
| 11,096,682 B2 | 8/2021 | Foerster et al. | |
| 2014/0222033 A1* | 8/2014 | Foerster ............. | A61B 17/0469 |
| | | | 606/144 |
| 2015/0112368 A1* | 4/2015 | Stewart ............. | A61B 17/0483 |
| | | | 606/144 |
| 2019/0000444 A1* | 1/2019 | Shelton, IV ..... | A61B 17/06109 |

* cited by examiner

SURGICAL INSTRUMENT FOR MANIPULATING AND PASSING SUTURE

CROSS-REFERENCE TO RELATED APPLICATIONS

This application is the U.S. national phase entry under 35 U.S.C. § 371 of International Application No. PCT/US2021/057032, filed Oct. 28, 2021, entitled "SURGICAL INSTRUMENT FOR MANIPULATING AND PASSING SUTURE," which claims benefit to and incorporates by reference in its entirety, U.S. Provisional Patent No. 63/106,713, filed Oct. 28, 2020, and U.S. Provisional Patent No. 63/219,671, filed Jul. 8, 2021; both titled "SURGICAL INSTRUMENT FOR MANIPULATING AND PASSING SUTURE."

FIELD

The present invention relates to a surgical instrument that can manipulate and pass suture through tissue.

BACKGROUND

Arthroscopic surgery involves the performance of surgical procedures through small openings and under visualization using an arthroscope. Access to a target tissue is normally provided through one or more portals formed directly in the patient's body or through one or more cannulas inserted into the patient's body through small incisions. A desired surgical procedure is carried out by a surgeon with elongated small diameter instruments inserted through these cannulas.

Often it is necessary to pass a flexible member, such as suture or suture tape through tissue during an endoscopic or arthroscopic procedure. This may mend a tear or close an incision in the tissue for example. Although this task is not uncommon, passing and retrieving suture through tissue can be challenging in these procedures where visualization and space is limited.

Various instruments have been developed to pass and retrieve suture through tissue during arthroscopic surgery. In some instances, an instrument with a pair of jaws may grasp the tissue and suture passed between the jaws and captured by one of the pair. However, these devices tend have difficultly accessing tight spaces, in some orientations. In other instances, suture passers with sliding grasping hooks have provided better access to these tight spaces, such as for example during arthroscopic access to the hip capsule. Preferably these devices provide a plurality of functions including piercing the tissue adjacent the repair, ejecting or pushing the suture away from the device, capturing the suture, holding the suture while allowing it to slide relative to the instrument, and/or holding the suture in a locked position, and thus preventing it from sliding. Some attempted solutions have compromised on at least one of these functions. Compromise may be required when handling a more delicate or fragile suture for example. Absorbable sutures are particularly difficult to protect from fraying while handing with sliding hook passers. There is therefore a need to provide an improved multifunctional suture passing and manipulating instrument that better manages smaller and more fragile sutures.

SUMMARY

Described herein is a suture manipulating instrument and method of use that passes suture through tissue. The instrument comprises a handle mechanism and a working distal end. The working distal end comprises a needle and a preformed inner member extending therethrough. The handle mechanism can be used to manipulate the needle and wire in a manner, which would allow the inner member to grasp and manipulate suture by pinning and/or trapping the suture against the needle. Improvements to reliably grasp and manipulate the suture without damaging the suture are disclosed. Improvements that reduce the need for user skill or compensating steps while managing the suture, including improved geometry and features of the inner member geometry in relation to the needle are disclosed herein, A first example embodiment of an instrument for manipulating and passing suture through a tissue is disclosed herein. The instrument includes handle end and a needle defining a distal end of the instrument. The needle includes a lumen up to and including a distal opening. The instrument also includes a hook axially moveable within the lumen and relative to the needle distal opening. The hook is axially moveable between a locked configuration in which the entire hook may be spaced proximally from the needle distal opening and locks a suture within the instrument and a capturing configuration in which the hook extends from the distal opening to capture or release the suture. The hook includes a distal leg configured to inhibit release of a captured suture therein. The hook distal leg has a length that extends across a diameter of the lumen, longer than the lumen diameter.

In some example embodiments, the entire hook may not be spaced proximally from the needle distal opening to lock the suture. For example, for larger diameter sutures, the hook may be partially disposed within the opening. In some embodiments, a hook distal facing surface defines a planar surface having a free end that is proximally spaced relative to a distal-most end of hook. The distal leg may be configured to bump up against the inner lumen surface of the needle to inhibits rotation of the distal leg induced by tension from the suture, and thereby prevent suture release. The hook distal leg may define a width that forms a lateral gap configured to frictionally engage the suture disposed between the needle lumen and hook distal leg, and deter sliding of the suture through the hook. The lateral gap may be approximately 0.015 inches on each side of the hook. The lateral gap may be between 0.013 inches and 0.018 inches. The needle distal opening inner edge surface may be broken to limit fraying of a suture. The needle distal-most end may define a sharp edge surface for piercing tissue.

Another example instrument embodiment is disclosed for manipulating and passing a suture through a tissue. The instrument includes a proximal end with a handle and a distal end that is a needle. The needle has a lumen extending up to and including a distal opening. The instrument also includes a hook, axially moveable along the lumen. The hook may axially side between an extended configuration and retracted configuration. In the extended configuration the hook is external to the lumen and to capture or release the suture. In the retracted configuration the hook is disposed within the lumen to hold the suture within the needle. The hook includes a distal-most leg that has a length and angular orientation relative to a diameter of the lumen when in the retracted configuration that is resists rotation of the distal-most leg and thereby prevents release of the suture held within the hook.

In some particular embodiments, the hook distal-most leg angular orientation placed free end of the distal-most leg proximally spaced relative to a distal-most end of the hook. The distal-most leg length may be greater than a diameter of the lumen. The hook distal-most leg may have a width that forms lateral gaps between the lumen and distal-most leg, when in the retracted configuration. These lateral gaps may frictionally engage the suture when in the retracted configuration, and therein deter sliding of the suture through the hook. This may lock the suture and prevent it from sliding around the hook. The lateral gaps may be 0.015 inches, which may lockingly hold a size 2.0 suture. The needle distal opening may include a graduated portion, that may reduce compression forces on the suture and thereby limit fraying of the suture. The graduated portion may include a length of increased diameter extending proximally from a distal-most edge of the needle. The graduated portion may reduce actuation forces required to move the suture and hook through the distal opening to the retracted configuration.

Another example embodiments instrument for manipulating and passing suture through a tissue is disclosed herein. The instrument includes a handle end and a needle defining a distal end of the instrument. The needle has a lumen with a distal opening. The instrument also includes a hook axially moveable within the lumen and through the distal opening. The needle lumen has a first diameter portion that extends proximally from the distal opening. A second diameter portion, that is larger than the first diameter portion, may extend proximally from the first diameter portion. The first diameter portion may funnel the hook with a suture captured therein into the lumen with a low compression force on the suture. The second diameter portion may hold the suture within the needle with either a sliding or locking hold.

In some example embodiments, the first diameter portion defines a curved counterbore portion. There may be a tapered or rounded transition between the first and second diameter portion. The first and second diameter portion may share an outer needle diameter that remains unchanged. The first diameter portion may define a thinner needle wall thickness than the second diameter portion. The first diameter portion may extends up until a proximal edge of the lumen distal opening. The second diameter portion may lockingly hold the suture within the needle.

Another example embodiment of an instrument for manipulating and passing a suture through a tissue is disclosed. The instrument includes a proximal end including a handle and a distal end that defines a needle. The needle has a lumen extending up to and including a distal opening. The instrument also includes a hook that is axially slideable along the lumen between an extended configuration and retracted configuration. The hook is external to the lumen configured to capture or release the suture when in the extended configuration. In the retracted configuration the hook is disposed within the lumen to hold the suture within the needle. The hook includes a distal-most leg with a length that extends from a first circumferential side surface of the lumen to a second circumferential side surface of the lumen, at axially spaced locations. The first and second circumferential side surfaces are on opposing sides of a longitudinal axis of the lumen. The length interacts with the circumferential side surfaces to prevent rotation of the distal-most leg when placed under tension from the suture and thereby prevents release of the suture from the needle when in the retracted configuration.

In some particular embodiments, the hook distal-most leg has a free end that is proximally spaced relative to a distal-most end of hook. The distal-most leg may have a distal facing planar surface. The distal-most leg length is greater than a diameter of the lumen. The needle distal opening may include a counter bore portion, configured to reduce fraying of the suture as it is funneled through the distal opening. The counter bore portion may also reduce actuation forces required to move the suture and hook through the distal opening. The hook has a lateral width that cooperates with an inner diameter of the lumen that is coextensive with the hook to define a mode of holding configuration on the suture. The mode may be a locking or a sliding hold configuration.

Another example embodiment of an instrument for manipulating and passing suture through a tissue is also disclosed. The instrument includes a handle end and a needle defining a distal end of the instrument. The needle includes an inner lumen extending therethrough and terminating with a distal opening. The instrument also includes a sliding hook axially moveable within said needle lumen and through the needle distal opening. The hook may be axially moveable between a locked configuration, a holding configuration, and a capturing configuration. In the locked configuration, the entire hook may be spaced proximally from the distal opening to lock a suture. In the holding configuration, the hook may be disposed at the distal opening configured to hold the suture, while allowing it to slide. In the capturing configuration, the hook extends away from the distal opening to capture or release the suture. The hook may include a 360-degree bounded loop portion. The loop portion has a first leg defining a distal facing surface that forms a portion of a hook pocket or suture grasping region and a second leg defining a proximal facing surface that cooperates with the needle distal opening to define a trajectory of the hook as the hook axially slides.

In some example embodiments, the hook pocket is sized to loosely capture a target suture. In the second configuration, a free end of hook may be disposed within the needle lumen and a portion of the hook, distal from the free end, may be disposed outside of the lumen. In some example embodiments, the needle distal end may define a graduated length, having an extent that is configured to funnel the suture into the needle lumen. The graduated length may include a counter bore that extends from the distal most edge of the needle lumen until at least a proximal most edge of needle opening edge.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1:
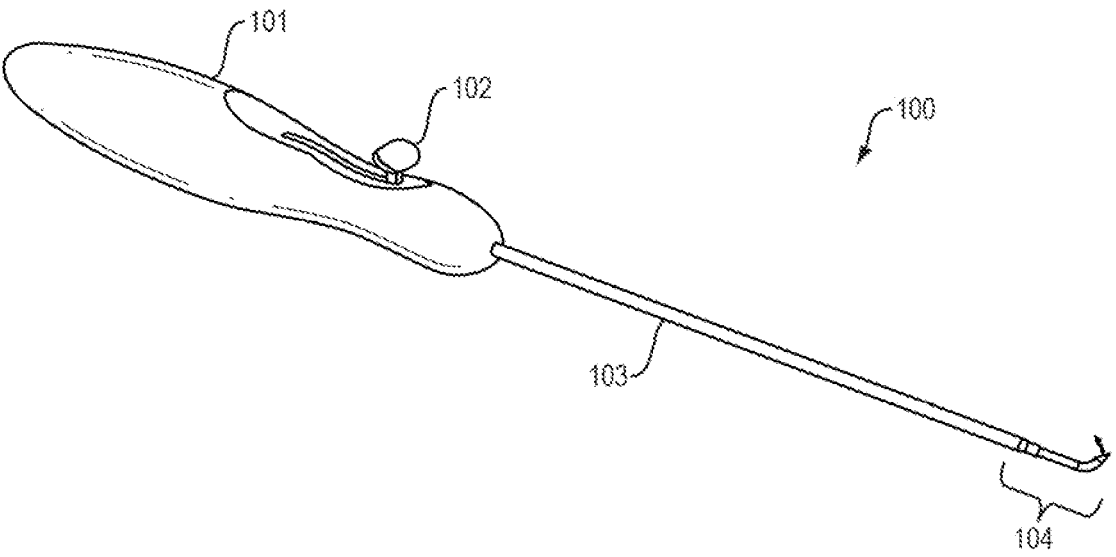
FIG. 1 illustrates a suture-manipulating instrument, in accordance with this disclosure.

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," "upwards," and the like is intended only to help in the clear description of the present disclosure and are not intended to limit the structure, positioning and/or operation of the disclosure in any manner.

Illustrated in FIG. 1 is a surgical instrument 100 in accordance with this disclosure, for manipulating and passing suture. Suture may include any flexible member or flexible strand, including but not limited to suture, suture tape, cable, ribbon, or wire. Instrument 100 comprises a handle 101, a lever, slide, or button 102 operatively coupled to the handle 101, an elongate shaft 103 extending distally from the handle, and a working end 104 defining a distal end of the instrument 100. Lever, slide, or button 102 (hereinafter slide 102) controls the suturing manipulating mechanism at the working end 104. Instrument 100 may manipulate suture in a similar manner to instruments disclosed in U.S. Pat. No. 10,265,062, titled "Surgical Instrument for Manipulating and Passing Suture", commonly assigned and herein incorporated by reference in its entirety. The instrument 100 may be used to pass and/or retrieve a suture as part of a tissue repair in a wide variety of applications including, for example, endoscopically or arthroscopically, for tissue associated with a hip capsule or shoulder (labrum or rotator cuff repair) for example.

Figure 2A:
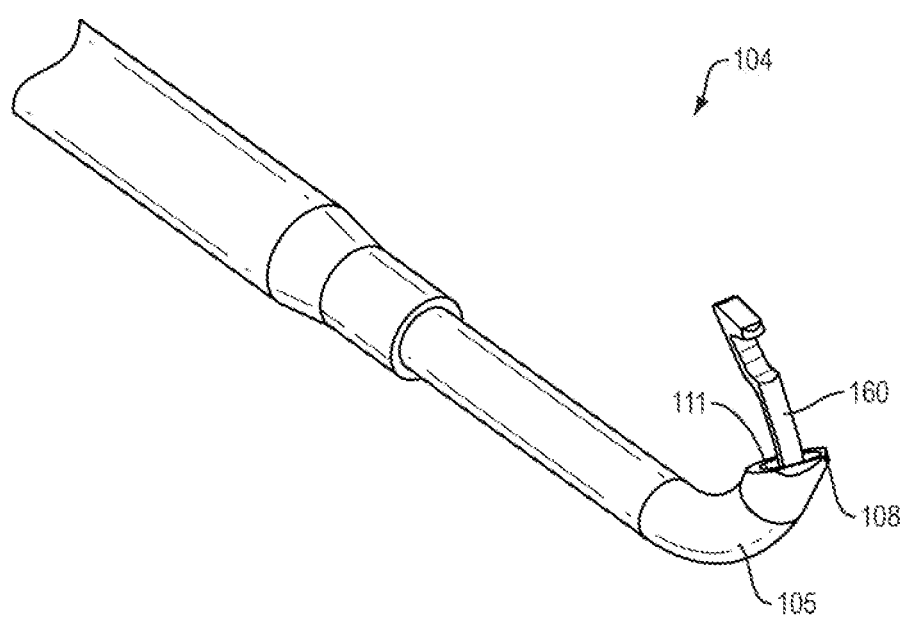
FIG. 2A illustrates a view of a working end embodiment of a suture-manipulating instrument, with the inner member in an extended configuration, in accordance with this disclosure.
Figure 2B:
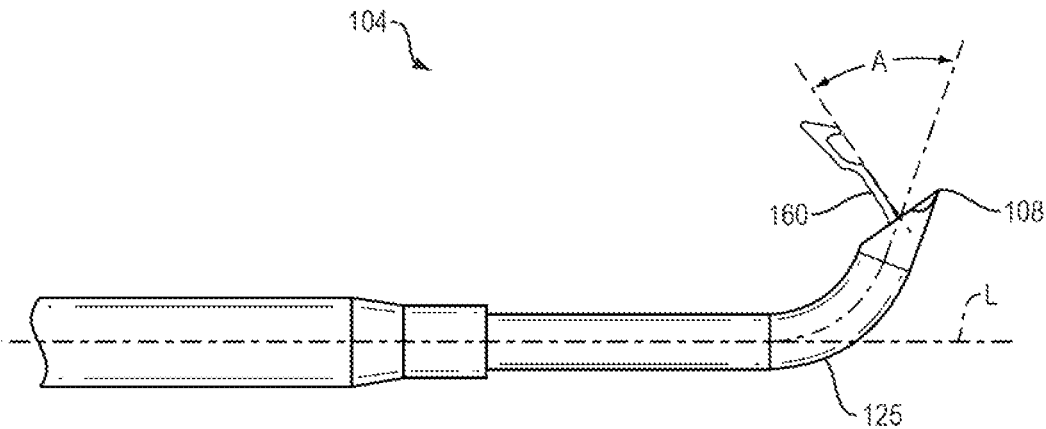
FIG. 2B illustrates a side view of the working end embodiment illustrated in FIG. 2A.
Figure 2C:
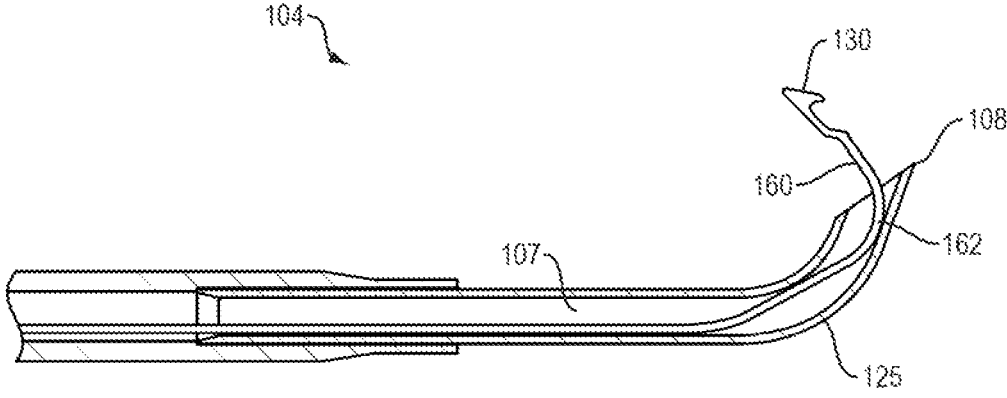
FIG. 2C illustrates a cross section view of the working end embodiment illustrated in FIG. 2A.

FIGS. 2A-2C illustrate a first embodiment of a working-end 104 of instrument 100. Working end 104 includes a needle 105 and an inner member 160 slidingly disposed within the needle 105. Needle 105 may have a needle point or tissue penetrating distal tip 108, configured to pierce tissue. Needle 105 includes a distal-most aperture 111 that may be an angled cut-off or beveled end. Needle 105 may include a bend 125, configured to improve access to the target tissue. The bend angle relative a longitudinal axis (L-L) of the handle and proximal shaft 103 is preferably between 12-90 degrees, and more preferably around 45-70 degrees. Needle 105 defines an inner lumen 107 that extends up to and include aperture 111. Inner lumen 107 is configured to cooperate with the inner member 160 to guide the trajectory of the inner member 160 as it axially sides and extends out and away from needle 105. Inner lumen 107 is also configured to cooperate with the inner member 160 to hold a suture when the inner member 160 is retracted within the needle 105. FIGS. 2A-2C illustrate the inner member 160 in the extended configuration, in that inner member 160 is in an axially distal position, extended through needle aperture 111. In this extended configuration, the inner member may catch or release a suture.

Figure 3A:
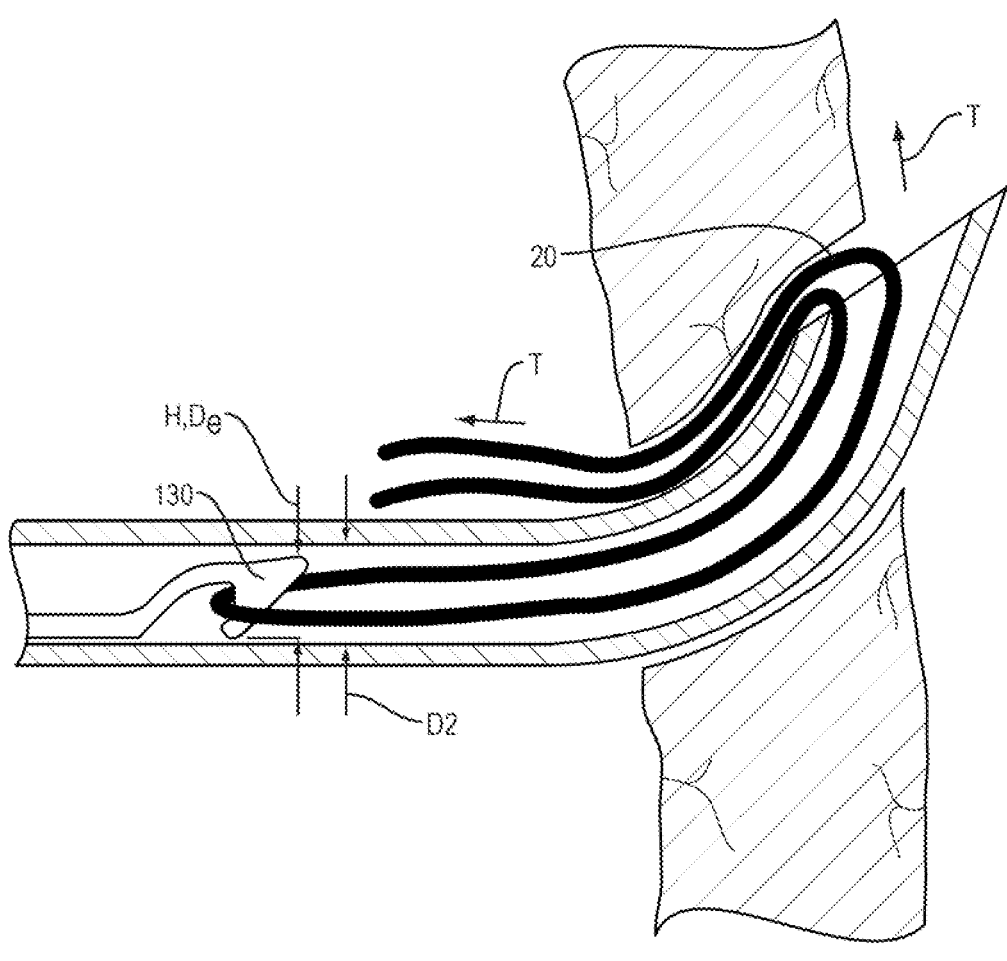
FIG. 3A illustrates a cross section of a working end embodiment extended through tissue and with the inner member in a retracted configuration, in accordance with this disclosure.

Inner member 160 is operatively coupled to slide 102 and is configured to axially slide along the needle lumen 107 via actuation of slide 102. Inner member 160 may slide and extend through aperture 111, to catch or engage a suture disposed near the aperture 111. Inner member 160 may be shaped to form a cavity to catch or engage a suture and retain the suture within the cavity while withdrawing the inner member 160 through opening 111 and along lumen 107. When retracted the inner member 160 cooperates with needle lumen 107 to capture the suture within the needle lumen 107. FIG. 3A illustrates inner member 160 in a retracted position, having captured a suture 20. While in this retracted configuration, the inner member 160 may be recessed within needle 105 and instrument 100 may be passed through tissue. In some embodiments the suture 20 may be held by the inner member 160 in the retracted configuration such that the suture 20 may not slide, herein-after termed a locking hold configuration. In some embodi-ments, the suture 20 may be held by the inner member 160 in the retracted or recessed configuration, such that it may still slide along lumen 107 while being held by the inner member 160, hereinafter termed a sliding hold configura-tion. In some embodiments, the inner member 160 may be withdrawn to be proximal of bend 125 in the retracted configuration.

Inner member 160 may be formed of a Nitinol or spring steel. Nitinol may withstand larger amounts of strain, and thereby offers larger variations in the trajectory of inner member 160 as it extends in and out of the needle 105. The distal section of the inner member 160 may have a pre-formed curve or bend, which the distal section assumes when the inner member 160 is in the extended configuration and the distal section is unconstrained by the lumen 107 of the needle 105. The curve or bend may comprise a first bend 162, which in the extended configuration, directs a distal end of the inner member 160 at a first angle "A" away from a needle axis, the needle axis extending through the needle towards the distal tip of the needle. Inner member 160 distal end is configured to grab a suture 20 and may terminate in the shape of a hook 130. Hook 130 is configured to coop-erate with the lumen 107 to hold the suture 20 and preferably holds the suture 20 without damaging it. With the more fragile sutures, damaging may occur with excessive com-pression on the suture 20.

Figure 3C:
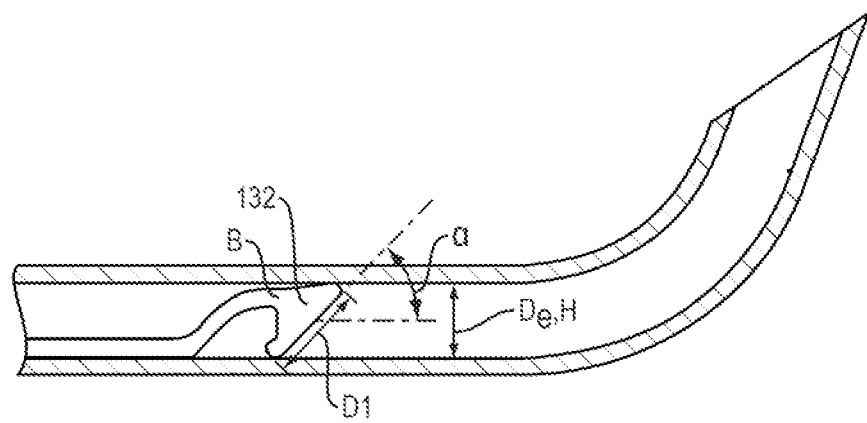
FIG. 3C illustrates a cross section of the working end embodiment along a plane parallel to longitudinal axis and laterally offset from a plane bisecting the working end, in accordance with this disclosure.
Figure 4A:
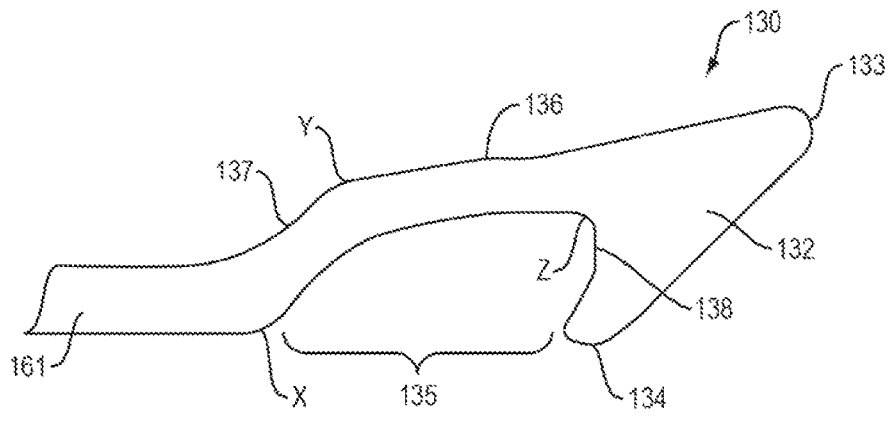
FIGS. 4A-4C illustrate various views of inner member hook of a suture-manipulating instrument, in accordance with this disclosure.

FIG. 4A illustrates a side view of hook 130. Hook 130 defines an open suture grasping cavity 135, defined by at least three sides. The cavity 135 is at least partially covered by lumen 107 to hold suture therein, illustrated in at least FIG. 3A. Hook 130 and lumen 107 may define a 360-degree bounded cavity when hook 130 is in the retracted configu-ration. Hook 130 defines three legs that define the three sides of cavity 135. A proximal leg 137 of hook 130 extends from inner member base portion 161. Proximal leg 137 is angu-larly offset from base portion 161. Inner member base portion includes first preformed bend 162. Proximal leg 137 is angularly offset by a first hook bend X. Proximal leg 137 may extend across a substantial portion of needle lumen inner diameter, when in the retracted configuration, best viewed in at least FIG. 3A and FIG. 3C. Second leg 136 may extend from proximal leg 137, at an angle defined by bend Y. Proximal leg 137 and second leg 136 may have similar cross-sectional widths and may have similar elasticity or flexibility. Second leg 136 may extend along a first side of a longitudinal axis L-L of needle lumen 107, defining a second or bottom side of hook cavity 135. Distal leg 132 may extend from a distal-most end of second leg 136. Distal leg 132 is angularly offset from second leg 136, defined by at least distal bend Z. Hook shape may be formed by bending or may be cut or molded to form bends X, Y and Z, or a combination of methods. Distal leg 132 is configured to inhibit inadvertent release of suture 20, even as the proximal leg(s) of the hook 130 and base portion 161 may flex. Distal leg 132 may have a larger cross section than the more proximal legs (137 and 136). Distal leg 132 may terminate in a free end 134 or nose. Hook distal leg 132 may define a larger cross section than proximal portion of hook 130, such that the distal leg 132 is stiffer than a proximal portion (136, 137) of hook 130. A proximal facing surface 138 of leg 132 may be orthogonally oriented relative a needle longitudinal axis L-L and may define a distal surface of hook cavity 135. This surface 138 is preferably substantially planar, or has limited concavity to limit the suture from cleating or recess-ing within a distal end of cavity 135. Cleating the suture may hinder removing the suture from within the hook, therefore a planar surface 138 may provide an easier release or removal of suture from the cavity 135.

Figure 3B:
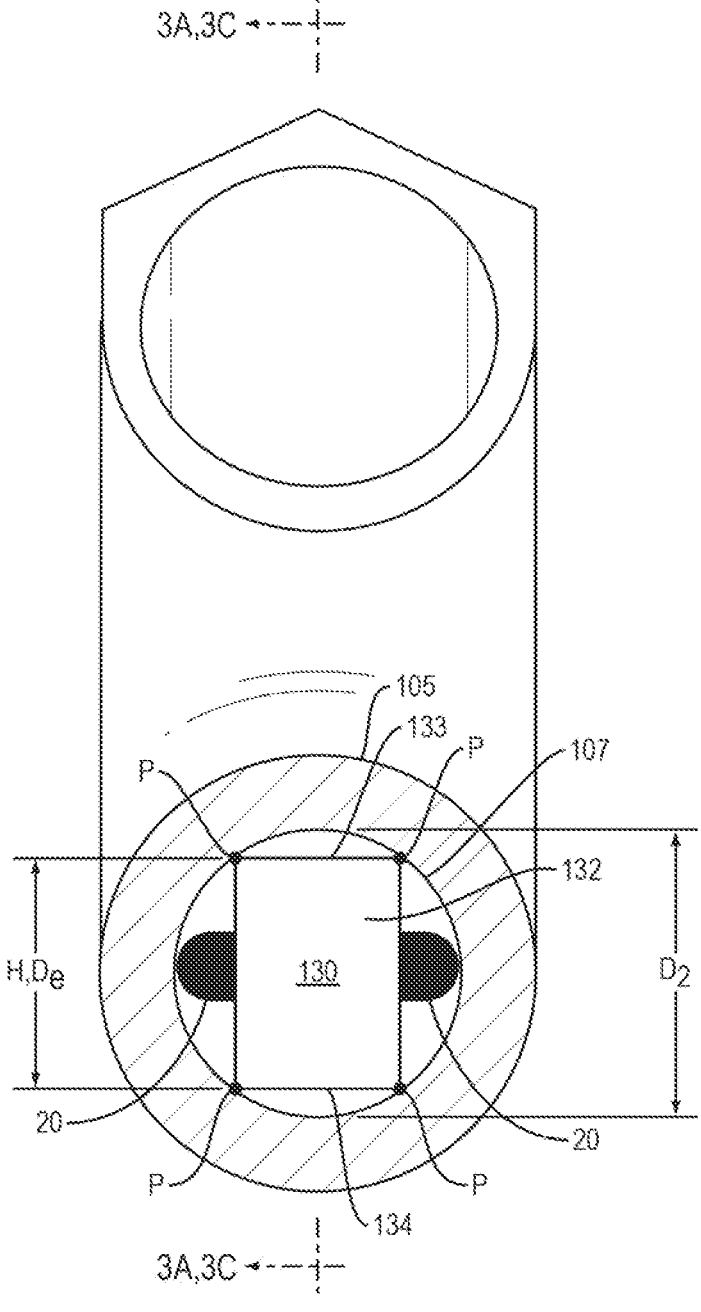
FIG. 3B illustrates a transverse cross section of the needle lumen, in accordance with this disclosure.

Referencing FIG. 3B, hook 130 and inner member 160 may have a substantially square or rectangular cross section. When disposed within a needle lumen 107 that is circular, (or a different shape to the hook cross section) points of intersection (P) between the hook 130 and inner lumen 107 may be offset from a bisecting plane of the device, extending along the device longitudinal axis. A cross section view through the needle longitudinal axis L-L along bisecting plane is shown in FIG. 3A. FIG. 3B is a transverse cross section to needle axis, with an end view of hook 130, and therefore hook 130 is viewed in projection. Hook distal leg 132 may define a projected height "H" that defines an effective diameter "De" of the lumen 107. Effective diameter "De" is equal to or smaller than inner lumen diameter D2. A cross section view parallel to bisecting plane through two points of intersection P is shown in FIG. 3C (with the suture removed) and in FIG. 3D. Best seen in FIG. 3C, distal leg 132 has a maximum length D1 that may be a linear length. Maximum length D1 is longer than effective length De. Maximum length D1 may also be longer than inner lumen diameter D2. Maximum length D1 is preferably at least as long as effective diameter "De". Length D1 may define a linear length between contact points P on opposing circum-ferential sides of the lumen 107. Leg 132 is therefore prevented from being rotated counter clockwise (with ref-erence to the FIG. 3C) via tension on the suture. Any rotation of leg 132 if there are any small gaps due to tolerancing only acts to reduce any gaps or further engage ends 133, 134 with the lumen surface. Hook 130 and more specifically hook distal-leg 132 therefore is configured to prevent release of suture. Hook distal-leg 132 has both a length and orientation that slides along the needle lumen while holding a suture within the hook, and also prevents inadvertent release from the hook.

Distal leg 132 is angularly orientated such that leg end 134 is axially spaced from opposing end 133. Points "P" are not necessarily points, but may be discrete surface zones that have circumferential length due to rounding or chamfering of hook edges. These point P are not all axially coincident lumen 107 as end 134 is disposed proximal of leg end 133. Four points "P" of intersection are shown. While there may be some points "P" that do not directly contact, due to tolerance variations and flexibility of the inner member 160, this does not preclude the underpinning theory behind the effective dimension De.

FIG. 3C is an elongate cross section taken through two points "P". This may also be an elongate cross section that is coincident with and parallel to a lateral surface of hook 130. Distal leg 132 has a longest dimension D1 that, in a neutral configuration, is orientated at an angle α to a longitudinal axis L-I of needle 105. Distal leg 132 may be in this neutral configuration when no external forces act upon the distal leg 132. External forces may come from tension (T) from a suture 20 held within hook 130, illustrated in in FIG. 3A. Angle α may range between 20-70 degrees and may preferably be about 45 degrees, when in the neutral configuration. Distal leg 132 extends from a first end 133 that defines the distal-most end of hook 130 up to and including free end 134.

Consider that the smaller the inner member 160 and hook 130, the smaller the needle diameter may be and the smaller profile the working-end 104 is. A smaller profile inner member 160 and hook 130, and thereby smaller profile working end 104 may be beneficial as it may form a smaller pierced hole size through the tissue. However, balancing the benefits of a smaller profile working-end 104 with an adequate size of suture capture cavity 135 to reliable capture and maintain hold of the suture 20 requires some balancing between hook stiffness and size of cavity 135. The hook 130 therefore may include proximal legs 136, 136 that are thin in cross section, maximizing the size of cavity 135 but potentially flexing when under external forces. Having a distal leg 132 that is larger in cross section may help increase stiffness of the hook distal end. Having a distal leg 132 longer than the lumen diameter or effective dimension De, as disclosed herein, may also provide a mechanism for maintaining hold on the suture 20 with an inner member, while maintaining a smaller profile working-end. While the proximal legs (136, 137) of the hook 130 together with the base portion 161 may be thinner and more flexible, the length and angle of the distal leg 132 relative to the lumen 107 may counteract any flexing of the hook 130 via interaction with the lumen 107.

Figure 3D:
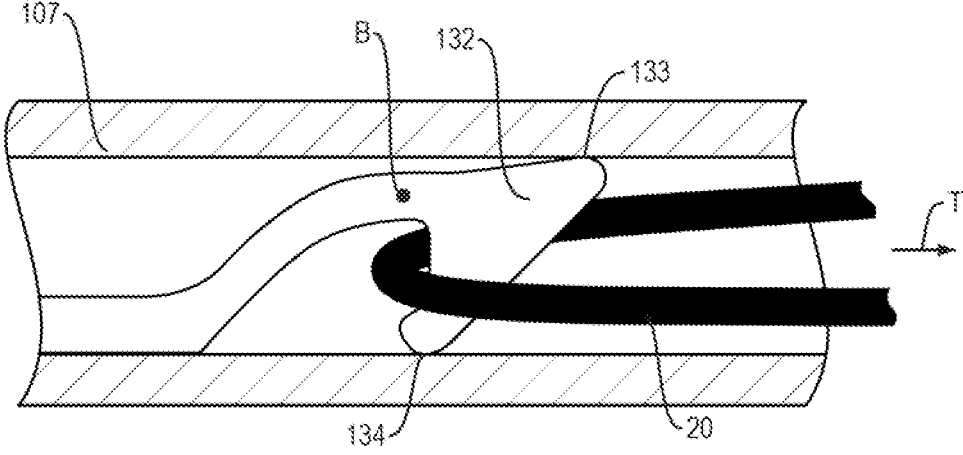
FIG. 3D illustrates a close-up view of FIG. 3C.

In the retracted configuration (either a locking or sliding hold configuration), suture 20 may apply a tension (T) on the hook 130 as the suture 20 and instrument 100 is pushed through tissue, for example. In the retracted configuration the preformed bend 162 may also apply a torque on distal leg 132, as a reaction to the forces that straightens the preformed bend 162. Tension T is illustrated in FIG. 3A. Referencing both FIGS. 3A and 3C, these external forces may act to rotate leg 132 in a counterclockwise manner about point "B" and increase angle α. However, because the distal leg 132 is longer than the De, any rotation is limited by the distal leg length D1. The distal leg 132 may therefore rotate up until two opposing ends (133, 134) of some portion of the distal leg 132 interferes with at least corresponding surfaces of the inner lumen 107. In the neutral configuration, the hook 130 may slidingly fit within needle lumen 107. The reaction forces from the preformed bend 162 may bias the distal-most end 133 against lumen surface. Should tension (T) from the suture 20 rotate distal leg 132, which may be reasonable given the small cross section and thereby relative flexibility of hook 130, the distal leg 132 may rotate counterclockwise, such that the free end 134 may move towards or engage with the inner surface of lumen 107. This rotation therefore inhibits any tension on the suture 20 from removing the suture 20 from hook 130. Furthermore, in some embodiments both ends of distal leg 132 may engage the lumen surface in the neutral orientation and tension on the hook 130 via suture 20 may be prevented or limited, wedging the hook 130 within the lumen 107 and maintaining hold of suture 20 therein. Therefore hook 130 and more specifically distal leg 132 is configured to provide a minimal profile hook that may flex with external forces from suture, while maintaining hold of suture 20 within lumen 107. FIG. 3D illustrates an example distal leg location with ends 133 and 134 in contact with inner surfaces on opposing sides of longitudinal axis of inner lumen 107.

In some embodiments, inner lumen 107 may not be circular in cross section and the term diameter defines an equivalent width of the lumen opening size 107. Preferably leg 132 is configured to rotate to a maximum angle α of less than 89 degrees. In some embodiments, leg 132 may rotate to a maximum angle α of less than 60 degrees. Inner member 160 and hook 130 is configured to elastically (and not plastically) deform such that upon release of any external forces, the hook 130 relaxes back towards the neutral configuration.

In use, the surgeon may capture the suture 20 with the hook 130, while the hook 130 and thereby inner member 160 is the extended configuration, and then draw the suture 20 into the lumen 107 to hold the suture 20. The suture 20 may be captured within the hook cavity 135. Withdrawing the inner member 160 may cover an opening to the hook cavity 135 with lumen 107 and thereby capture the suture 20 within hook 130. The needle distal tip 108 may then puncture a tissue, placing the needle opening 111 and portion of suture 20 held within the needle 105 by hook 130 on the other side of this tissue. During puncturing, a tension on the suture may act to remove the suture 20 from the hook cavity, the distal leg of hook 130 configured such that the tension (T) moves a distal leg 132 of the hook to inhibit the suture from escaping. During puncturing, a tension on the suture 20 may elastically deform hook 130. This may rotate a distal leg 134 of hook 130, from a neutral configuration. Rotation of distal leg 132 may continue until each end of leg 134 (132, 133) abuts, one each, an opposing surface of lumen 107. Once tissue is punctured, tension from the suture may reduce and leg 134 may relax towards the neutral configuration. The hook 130 may then be advanced out of the needle opening 111 to eject the suture 20.

As disclosed earlier, hook 130 may be configured to form a locking hold or sliding hold of suture 20. This may be defined at least partly by the lateral gaps between lateral sides of hook 130 and lumen 107. Lateral gaps are preferably configured to define the category of hold on the suture 20, while not overly compressing the suture 20, which may damage the suture. This is especially the case for the more fragile absorbable category of sutures.

Figure 4B:
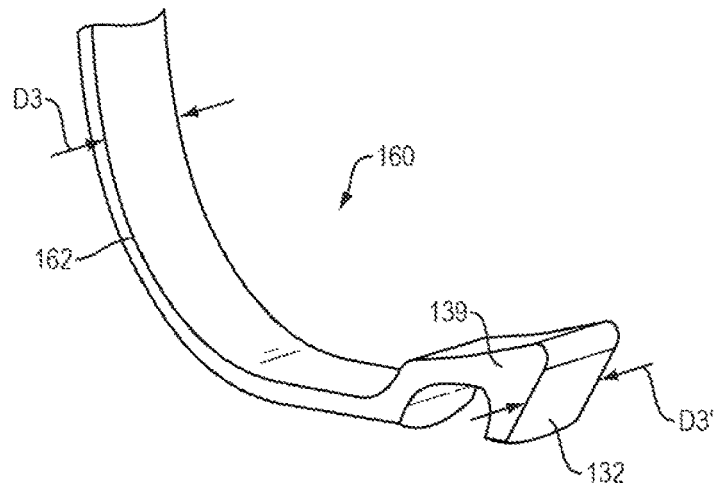
Figure 4C:
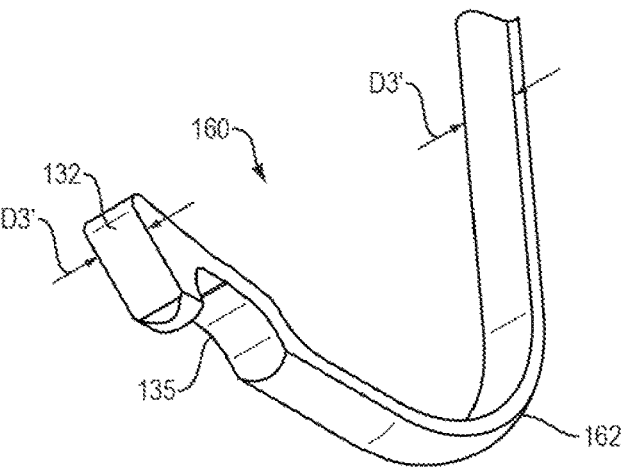

Turning now to FIGS. 4A-4C, various features of the inner member 160 are disclosed. In this embodiment, inner member 160 may define a uniform width D3 along its entire length. Most relevant to the category of hold on the suture 20 is the lateral width D3' of distal leg 132, which in this embodiment is similar to the width along the inner member D3. Lateral width D3 and D3' is preferably smaller than inner lumen diameter so that inner member 160 may axially slide therealong while holding a suture. Of note, this disclosure includes a cylindrical needle lumen cross section. Should the needle lumen be oblong, the term "diameter" may also include an opening size that lies along the same plane as lateral width D3 and D3' configured to define a lateral gap for the suture 20 to extend through.

Figure 5:
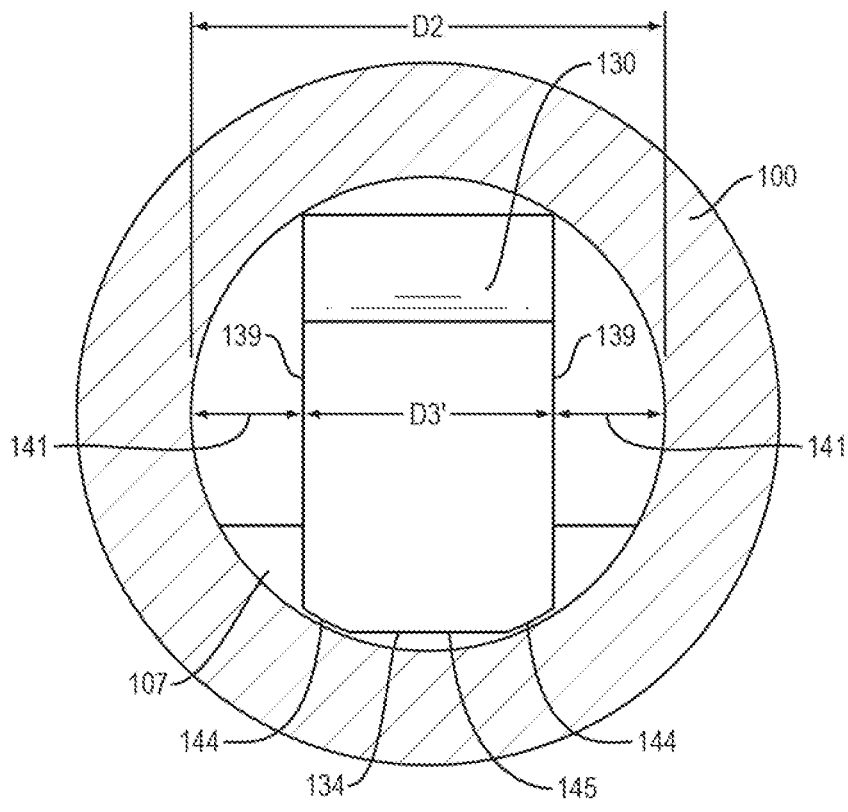
FIG. 5 illustrates an end view of an inner member hook relative to the needle lumen of a suture-manipulating instrument, in accordance with this disclosure.

FIG. 5 illustrates a cross section illustrating hook lateral width D3', lumen 107, diameter D2 and the resultant bilateral gaps 141. As shown, gaps 141 are equivalent in size. In alternative embodiments, gaps 141 may be different, and the hook may be asymmetric within the needle 105, to frictionally hold one side of the suture 20 more than the other side. This may make manipulation of the hook easier. The hook lateral width D3' may be uniform along leg 132, configured to create a target interference between the suture 20 that extends between the lateral surfaces 139 of leg 132 and inner lumen surface of the needle 105.

In embodiments configured to hold suture in a locking hold configuration, this target interference may inhibit suture sliding. However, gap 141 is also configured to limit overly cinching or compression on the suture, which may damage the suture. Gap 141 is configured to provide some frictional hold on the suture 20. This may limit the forces on the leg 132 and resultant flexing of hook 130 as disclosed herein. The hook cavity 135 therefore acts like less of a pulley and the suture 20 is hindered from slipping around leg 32. At the same time, the interference is limited to abate damage to the suture 20 when in the lumen 7. For example, the lateral width D3' of the distal leg 132 may be 0.033"±0.002" and the inner diameter (D2) or opening size of the lumen 107 may be 0.064 inches. Each gap 141 may therefore be approximately 0.015 inches, at its maximum. This may be preferable for a size 2 suture that may have an average diameter of 0.021 inches.

In other embodiments, this gap 141 may allow suture sliding and thereby provide a sliding hold on suture. In this embodiment, hook 130 may have a lateral width D3' that forms resultant lateral gaps 141 that may slidingly hold the flexible member 20 within the needle lumen 7. In this example, the hook lateral width D3' may be 0.010 inches (±0.002") for a corresponding lumen opening size of 0.064 inches. Each gap 141 (one either side of hook 130) may therefore be approximately 0.027 inches. This may be preferable for a sliding hold of a size 2 suture that may have an average diameter of 0.021 inches.

Holding the suture 20 while the hook 130 is proximally retracted from the entire needle opening 111, forms a loop length of suture 20 that is captured and stored within the needle 105 while inserting the needle distal tip 108 through tissue. This loop length is fixed in length provided the hook 130 does not move. If the suture is held with a sliding hold, the loop length may not change in overall length, but may slide around the hook 130 and along the needle lumen 107 distally extending therefrom. The loop length has a length corresponding to approximately twice the distance between the opening 111 and the suture loop end that wraps around the distal leg 132. Stated in another way, this loop length corresponds to about twice the distance the hook 130 is withdrawn along the needle 105 from the needle opening 111. Ejecting a length of suture 20 on the other side of the tissue after insertion releases the loop of suture 20 for easier manipulation and capture.

Hook end 134 may be configured to slide along lumen surface along two discrete lateral disposed surfaces 144 of end 134. These may correspond with points "P" disclosed earlier. These surfaces 144 may be chamfered, contoured or rounded. These surfaces contact the lumen 107 and inhibit the suture 20 from being drawn under the hook end 134. However, in order to improve sliding of inner member 160 along lumen 107, the surfaces 144 are lateral separated by clearance 145. End 134 may define clearance 145 that is centrally aligned between the bilateral surfaces 144 to form two discrete sliding rails, laterally separated to improve sliding of inner member along lumen 107. Surfaces 144 may contact lumen 107 during sliding and while in the neutral configuration, as disclosed herein.

In alternative embodiments (not shown) needle 105 may include a reduced internal diameter along a length portion of the lumen 107 in a discrete location along the needle 105. For example, the lumen 107 could include a detent or localized kink or deformation to needle 105. This detent example may further alter and deform or apply pressure to the hook 130, altering its grasp configuration on the suture, so as to further lock it, or allow it to slide, depending on the hook location and interaction with the detent. For example, a localized kink may form a smaller lateral opening size, such that when the hook 130 is axially coextensive with this kink, the lateral gaps 141 are reduced, locally. The suture 20 may therefore be held in a locking hold configuration when the hook is axially coincident with this kink, and help in a sliding hold configuration when the hook 130 is axially spaced from this kink. Alternatively, lumen 107 could include holes or reliefs through a portion or entire thickness of needle wall at discrete locations that may operate to define axial locations that slidingly hold the suture 20 when the hook lateral surface 139 is axially coincident with these reliefs.

In some instrument embodiments, the inner diameter (D2) of needle 105 may be incrementally increased along the needle length. This may provide both a locking and a sliding hold configuration or mode in a single instrument, both configurations provided with the hook 130 proximally spaced from the opening 111 and thereby both modes configured to eject a suture loop length from the needle 105. Needle 105 may have a first mode portion having first internal diameter that extends from the needle opening 111 proximally a first length along the needle longitudinal axis. Needle 105 may have a second mode portion, different in internal diameter to the first portion that extends for a second length, proximally from the first mode portion. The first mode portion may be configured to interact with the hook 130 and suture 20 in either a sliding or locking hold configuration. The second mode portion may be configured to change the mode of holding of the suture 20 to the other mode than the first mode portion. The second mode portion may be configured to hold the suture in a different mode than while the hook 30 is substantially within the first mode portion. The first length may be between 0.5-2 inches long, along the needle axis, measured from needle opening 111. The second length may extend along the remaining length of the needle lumen 107 and may have a distal most edge that is 0.5 inches from the needle opening 111.

In use, the surgeon may capture the suture 20 with the hook 130, while the hook 130 and inner member 160 is the extended configuration, and then draw the suture 20 into the lumen 107 to hold the suture 20. The suture 20 may be captured within the cavity 135. The needle distal tip 108 may then puncture a tissue, placing the needle opening 111 and portion of suture 20 held within the needle 106 on the other side of this tissue. The hook 130 may then be advanced out of the needle opening 111 to eject the suture 20. While puncturing the tissue, the hook 130 may be disposed a first distance from the opening 111 and along a length of the needle 105 defining a first internal diameter configured to slidably hold the suture 20. Ejecting the suture 20 ejects a suture loop length have a length defined by the first distance. The instrument 100 may then be withdrawn and passed through a different portion of tissue before capturing the suture 20 with the hook 130 in the extended configuration. The suture 20 may then be withdrawn into the needle 105 a second distance from the opening 111, engaging the hook 130 with a second mode portion of the needle 105. This second mode portion may lock the suture 20 within the needle 105. The instrument 100 may then be withdrawn, while lockingly holding the suture 20. The instrument handle 101 may include a control button, which may provide feedback to the user as to which mode the suture 20 is being held in. For example, the control button 102 may axially slide and may require a change in direction or a higher force of actuation to move into or out of each mode. For example, the user may feel a detent or some tactile feedback upon moving from one mode to the other. In another example, the sliding button 102 may slide in a first direction to slidingly hold the suture 20 and may require a jog or shift in sliding direction hold the suture 20 in a locking hold configuration.

Figure 6A:
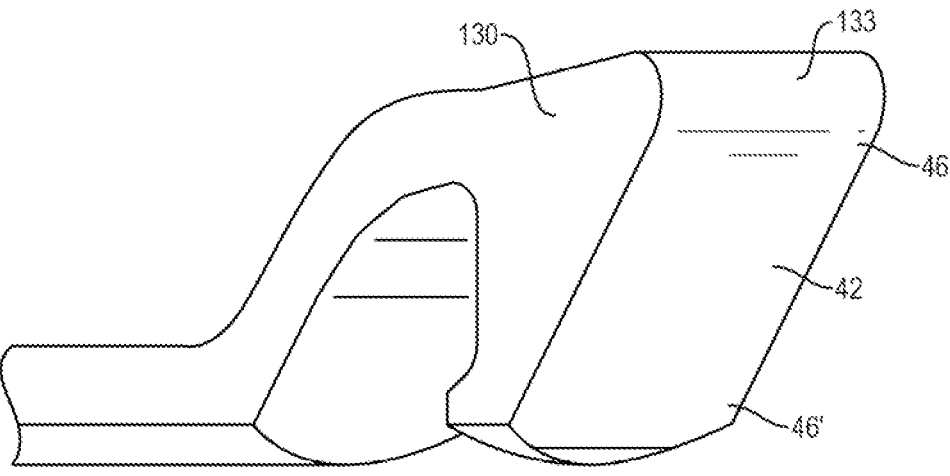
FIG. 6A illustrates a perspective view of another inner member hook of a suture-manipulating instrument, in accordance with this disclosure.
Figure 6B:
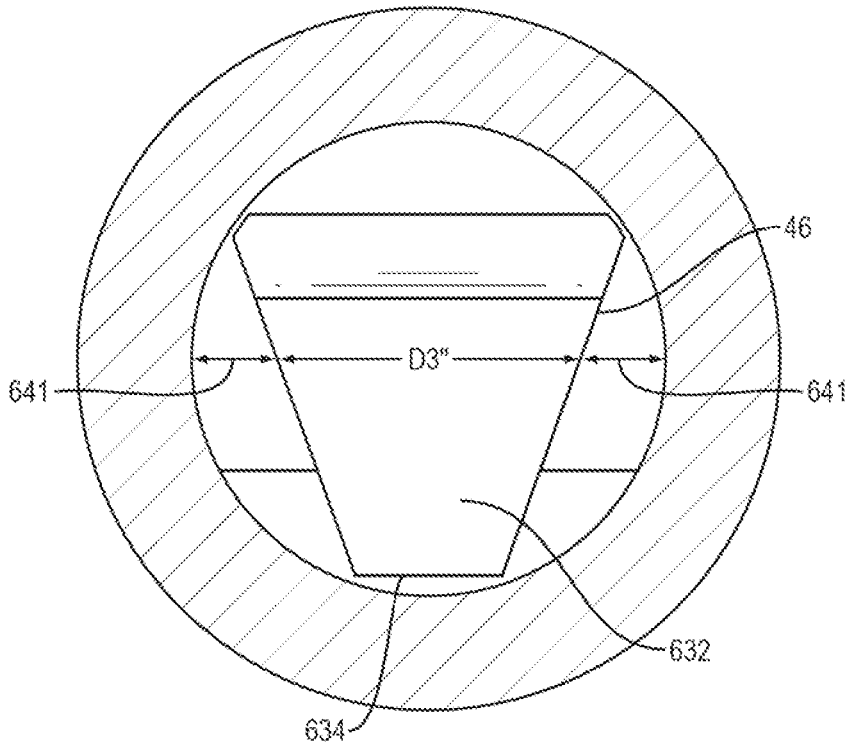
FIG. 6B illustrates an end view of the hook illustrated in FIG. 6A within the needle lumen of a suture-manipulating instrument, in accordance with this disclosure.

In an alternative hook embodiment, illustrated in FIGS. 6A and 6B, hook distal leg 632 may be tapered, having a tapered lateral width D3", tapering from its largest width dimension at the leg distal-most end 633 to a smaller width dimension at the nose 634. Hook leg 632 is configured to form a tapered lateral gap 641 between lumen 107 and leg 632 on both sides of leg 632. Both gaps 641 may be equivalent in size and shape to each other, but vary along their length, defined by taper. The taper is configured to create a target interference on the suture 20 extending between lateral surface of the leg 632 and lumen 107 of the needle 105. In this embodiment, the gap 641 varies along its length and the maximum gap portion is configured to create a target interference on the suture 20. The taper may advantageously improve suture capture. Taper forms a narrower nose 134, which may hook around suture more easily.

At least some embodiments of instrument may be configured to reduce damage to the suture 20, because of edges along the entrance aperture 111 to needle 105. Some more fragile sutures, such as the absorbable suture category may be more prone to fraying and yet may be the preferable suture for some tissue repairs. In addition, as instruments become smaller in profile with thinner walls, the available space for rounded edges or chamfers is also reduced. Furthermore, the edge surface of aperture 111 has contrary requirements in that it may require a sharper edge surface for piercing tissue while also require more blunt or rounded surfaces for suture to slide along as it is drawn through and held with the needle 105.

Figure 7:
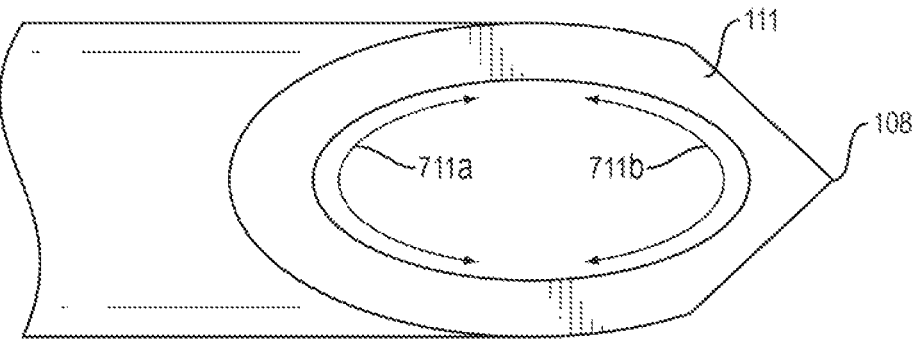
FIG. 7 illustrates a working end embodiment of a suture manipulating instrument, in accordance with this disclosure.

With reference to FIG. 7 illustrating a top down view of aperture 111, in some embodiments the needle opening 111 may include a blunter or more rounded edge along proximal portions 711a of edge surface of opening 111 and a less blunt edge surface along distal portions 711b. Opening 111 may be rounded with an edge break that varies around the edge surface that define opening 111. As the suture 20 is withdrawn into the lumen 107, it may be compressed against this proximal segment 711a. In some embodiments, edge surface portion 711a may include a radius break between 0.005-0.010 inches, or a chamfer may extend across 75% of the needle wall. In some embodiments this radius break may extend around the entire opening 111 and then distal portion 711b may be ground, to sharpen the tip 108.

Figure 8:
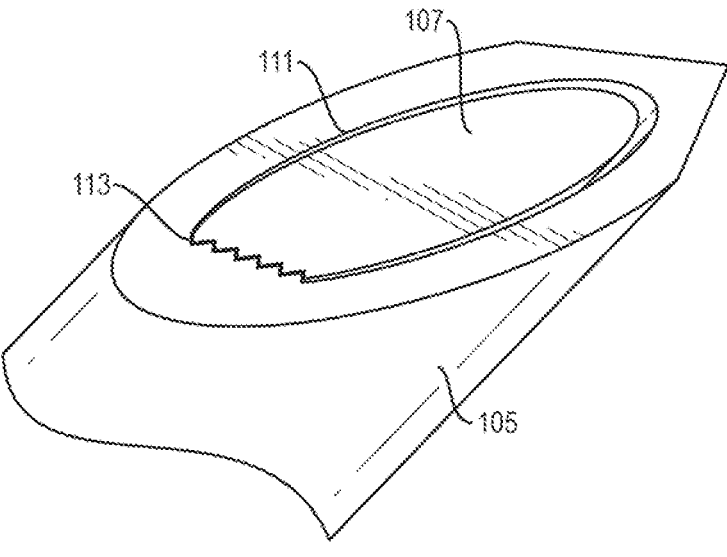
FIG. 8 illustrates a view of a working end embodiment, with an example notch formed thereon, after some actuation of the inner member.

The inventors have found that repeated actuation of the preformed inner member 160 may deform or cut into the thin walls of the needle 105. This may occur as the inner member 160 rides along an edge surface of the entrance aperture 111, exacerbated by a smaller profile instrument that will inherently have thinner needle walls. This repeated actuation may form sharp edges or a notch 113 at the entrance aperture 111 to the needle 105 where the inner member 160 predominantly rides. This notch 113 is represented in FIG. 8, with the inner member 160 removed to simplify illustration. As shown, notch 113 may form across a proximal most edge of aperture 111. Consider now the action of a suture 20 as it is funneled into the small needle lumen 107 by the inner member 160. In order to provide a smaller profile needle 105 that secures the suture 20 therein, there is not a great deal of clearance between the inner member 106 and needle lumen 107, which may compress suture 20 between the inner member 160 and lumen 107. The inventors have found that this funneling and compression of the suture 20 into the tight space between the needle lumen 907 and inner member 160 while entering the aperture 111 not only requires high actuation forces, but may fray or cut the suture 20, should it be pressed against a sharp edge, such as notch 113. Edge breaks may temporarily alleviate the issue, such as chamfers or bead blasting; however may be insufficient for smaller needle profiles after repeated cycling of inner member 106 through aperture 111.

Figure 9A:
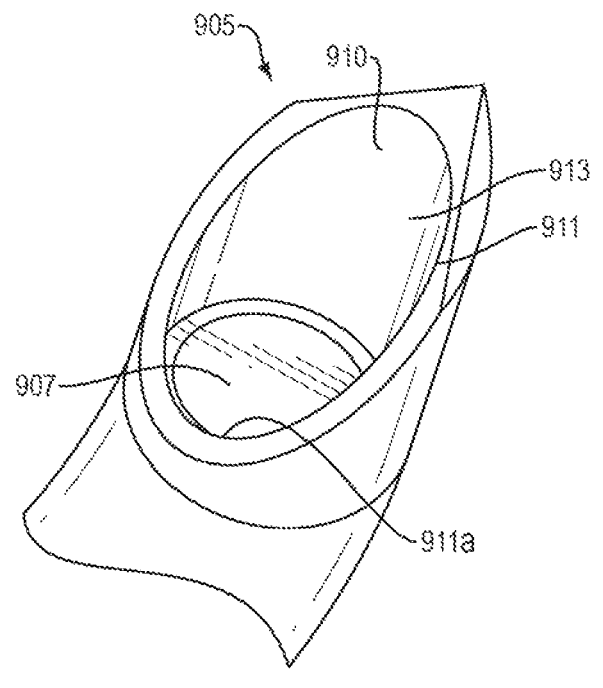
FIG. 9A. illustrates a perspective view of a needle distal end embodiment with a graduated opening, in accordance with this disclosure.
Figure 9B:
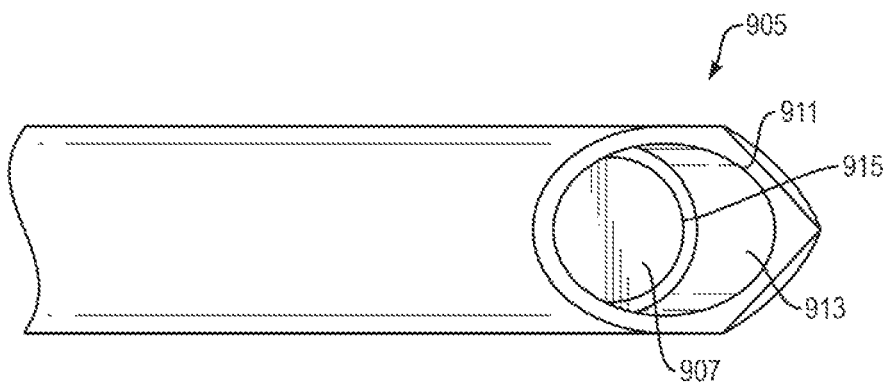
FIG. 9B. illustrates a top view of the needle distal end embodiment with a graduated opening, in accordance with this disclosure.
Figure 9C:
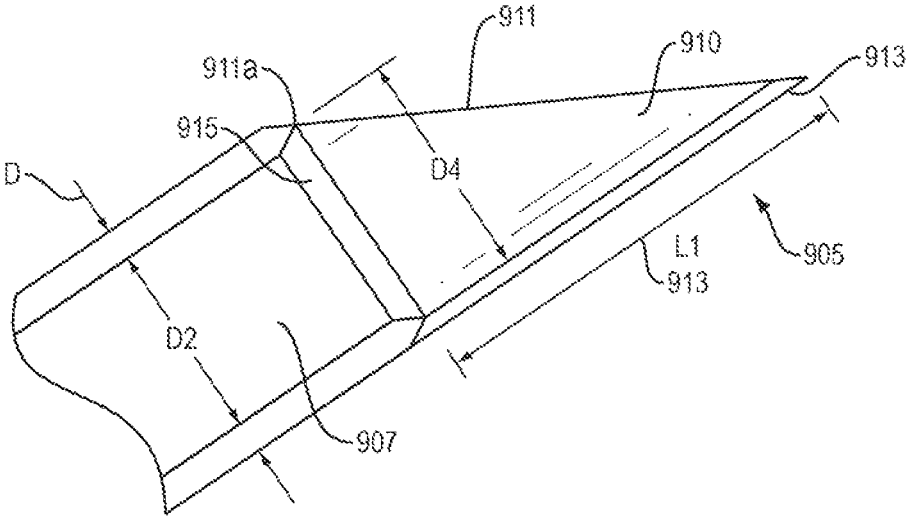
FIG. 9C. illustrates a cross section view of the needle distal end embodiment with a graduated opening, in accordance with this disclosure.

A needle embodiment that may mitigate formation or the effect of a sharp edge 113 is illustrated in FIGS. 9A-9C and 10A-10B. (FIGS. 9A-9C illustrate a needle distal end 905 absent an inner member 160 to simplify figures.) This needle embodiment 905 may be similar to needle 105 and may cooperate with an inner member 160 and hook 130 in a similar fashion to previously disclosed embodiments. The inventors have found that a proximal edge 911a may become notched during use. While manipulating the suture 20, it may become wrapped around the inner member 160 and be compressed between leg 136 and notched edge. Needle distal end 905 therefore includes a graduated or funneled portion 913, that may reduce damage to the suture 20. The needle distal end 905 may have a consistent outer diameter along the entire needle distal end 905, maintaining a low profile for minimizing insertion hole size through the human tissue. The inner lumen diameter however may transition from a larger opening size D4 along the graduated portion 913 for funneling the suture 20 into the needle lumen 907, to a second, smaller inner lumen diameter proximal graduated portion 913. Second inner lumen diameter may be similar to lumen diameter D2, disclosed in embodiments herein, and may be configured to cooperate with hook 130 to hold the suture 20 within the needle 907, either in a locking hold or sliding hold configuration. The graduated portion 913 may be slightly larger in diameter, configured to reduce actuation forces as the suture 20 enters the needle 905.

Graduated portion 913 may be in the form of a counterbore 910. Counterbore 910 may extend from a distal most edge of lumen 907 and extend proximally therefrom. Counterbore 910 may be continuous with the entire aperture 911. Counterbore 910 may extend from a distal most edge of needle 905 and extend proximally therefrom. Counterbore 910 may extend proximally up to at least a proximal edge 911a of opening aperture 911. Counterbore 910 may form the internal surface of needle 905, continuously around 360 degrees (angular) of needle lumen 907. Counterbore 910 extends a length L1 defining the graduated portion 913 having a first inner diameter D4 (or cross section width) of needle lumen 907. A second, smaller inner diameter lumen D2 extends proximally therefrom. The transition 915 between the two diameters (D2, D4) may preferably be rounded or tapered, to reduce damage to the flexible member 20. The distal extent of the lumen 907 with the second smaller inner diameter D2 may be proximally spaced, or axially coincident with a proximal edge 911a of opening 911. The second inner diameter D2 may operatively interact with the inner member 160 to lock a flexible member 20 within needle distal end 905. The first inner diameter D4 is configured to funnel the flexible member 20 through opening 911 with reduced compression. First inner diameter D4 may engage but preferably not lock the flexible member 20 when hook 130 is axially coincident with graduated portion 913. All diameters are perpendicular to the needle longitudinal axis, the needle longitudinal axis extending through the needle distal end towards the distal tip 108 of the needle. The term diameter may refer to a corresponding cross section width or height, should the needle 905 be oblong in shape.

As way of an example, with reference to FIG. 9C and FIG. 5, the hook lateral width of the distal leg 132 may be 0.033"±0.002" and the proximal or second inner diameter D2 of the lumen 907 may be 0.065 inches. Gap 141 may therefore be approximately 0.016 inches, while hook 130 is disposed within the second internal diameter D2 portion. This may be preferable to compress and lock a size 2 suture that may have an average diameter of 0.021 inches. Along the graduated length portion 913, the counterbore 910 may be formed with a 0.078" ball end mill. Therefore, at the opening 911 and along the graduated length portion 913, the counterbore may define a 0.078 inch diameter. Gap 141 may therefore be approximately 0.028 inches each side of the hook 130 within the first internal diameter portion D4 that is larger than a preferred suture such as a size 2 suture with an average diameter of 0.021 inches. This may be preferable to loosely engage and funnel a size 2 suture that may have an average diameter of 0.021 inches.

Preferably, the outer most diameter "D" of needle 905 remains uniform along entire needle distal end 905, such that along the graduated length 913, the needle wall thickness may be reduced. As an alternative to a counterbore 910, the distal tip of needle diameter D along the graduated length 913 may be slightly enlarged, thus enlarging both the first inner diameter D4 and the outer diameter D. In this example, needle 905 would create a larger insertion conduit through the tissue, which may not be preferable. In other embodiments, graduated length 913 may be reamed out in multiple step-wise counterbores of varying diameters sequentially reducing the inner lumen diameter, to improve the transition to the smaller diameter D2. In other embodiments, a tapered end mill may form a gradually tapering opening.

Figure 10A:
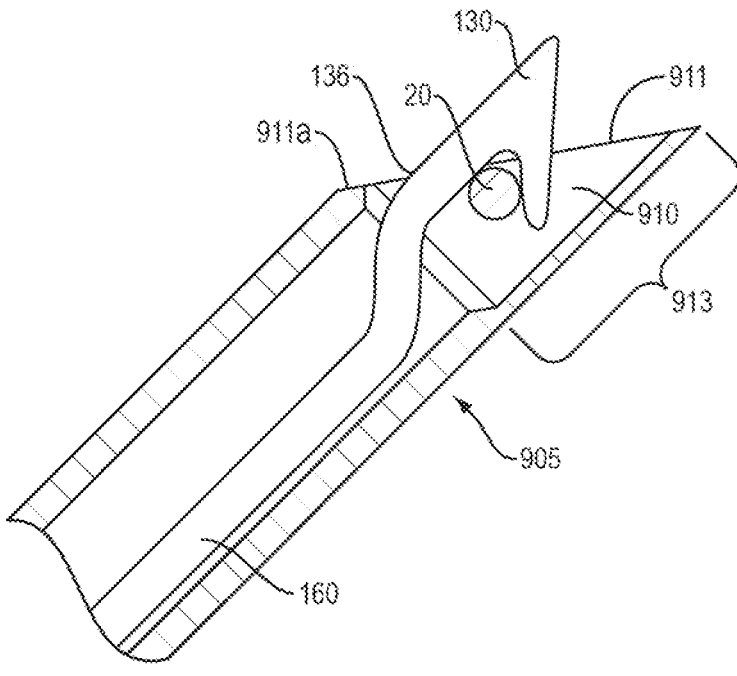
FIG. 10A illustrates a simplified cross section of the needle distal end illustrated in FIGS. 9A-9C with the inner member and suture within the graduated length, in accordance with this disclosure.
Figure 10B:
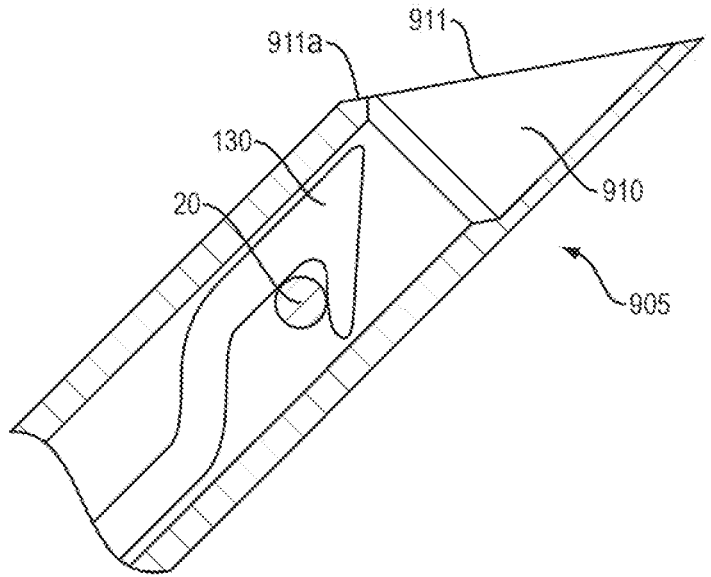
FIG. 10B illustrates a simplified cross section of the needle distal end illustrated in FIGS. 9A-9C with the inner member and suture proximally spaced from the graduated length, in accordance with this disclosure.

FIGS. 10A and 10B illustrate the steps of drawing the suture member 20 into the needle distal end 905. The distal end 905 is shown without a bend such as bend 125, as a simplified representation of the relative locations of the graduated portion 913, hook 130 and suture 20. FIG. 10A illustrates a funneling position, wherein an apex or bight of suture member 20 is captured by the hook 130 and has been drawn into the graduation portion 913. Inner diameter D4 of graduation portion 913 is configured to funnel the suture 20 with a reduced compression to avoid fraying of flexible member 20 as it rides along any sharp edges formed or inherent at opening 911. Graduated length 913 may be a counterbore 910 that extends up to a proximal edge or aperture 911a. While in the funneling position, the suture may slide through the hook 130. FIG. 10B illustrates the hook 130 in the locking or sliding hold configuration depending on at least the hook configuration as disclosed herein. In this configuration, the entire hook 130 is proximally spaced from the proximal end of graduated portion 913. The lengths of suture 20 may extend through aperture 911, which may have a notch 113; however the hook 130 is absent in the graduated portion 913, and therefore not compressing the fragile suture against any notch 113 that may have been formed.

Figure 11:
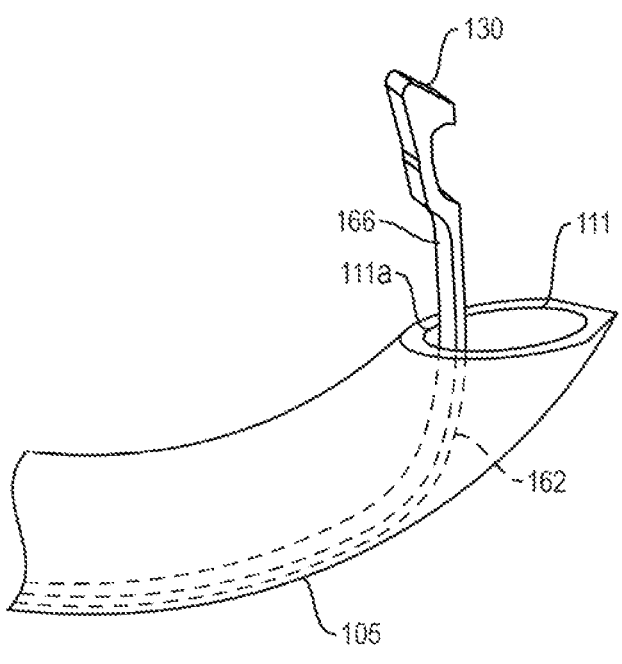
FIG. 11 illustrates another working end embodiment, in accordance with this disclosure.
Figure 12:
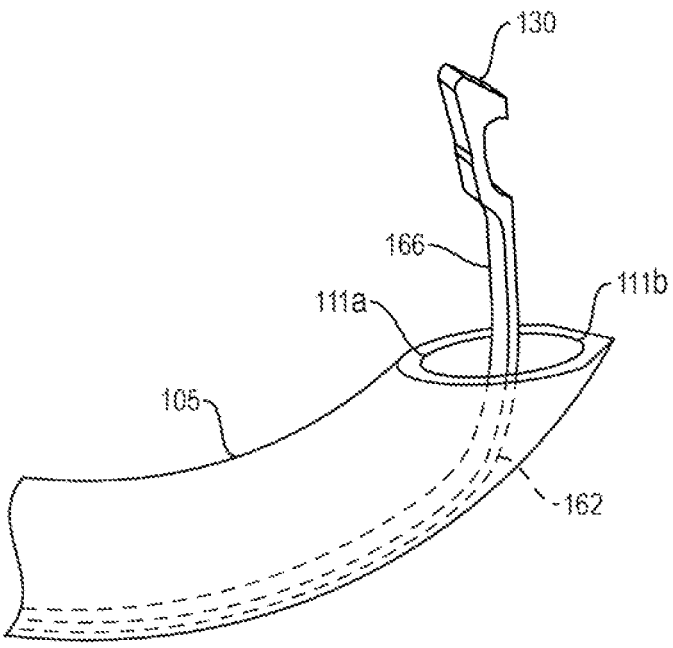
FIG. 12 illustrates another working end embodiment, in accordance with this disclosure.

FIG. 12 illustrates an instrument embodiment configured to improve ejection the suture 20 from the needle 105. Turning briefly to FIG. 11 as reference, when sutures are small or formed of a material that is more likely to fray or distort, the suture may become locally deformed while pinched within the needle 105. The inventors have found that when the suture is more fragile and/or has been deformed and therefore locally weakened or malleable, it may tend to migrate around the sides of the inner member 160. This may cleat or snag the suture 20 behind the inner member 160 and further damage it. This may also trap the suture between a proximal surface 166 of the inner member 160 and a proximal edge 111a of opening 111, frustrating release of the suture 20 from the working end 104. As the inner member 160 deploys, it may engagingly slide along proximal edge 111a up until the first bend 162 relaxes to the preformed shape. The first bend 162 assumes this relaxed, preformed shape when the inner member 160 is in the extended configuration and the bend 162 and distal section of inner member 160 is unconstrained by the lumen of the needle 105. The preformed shape comprises a first bend 162, which directs the distal section of the inner member 160 including the hook 130 at a first angle "A" laterally away from a needle axis, the needle axis extending through the needle towards the distal tip of the needle. Inventors have found that axially moving the inner member 160, including the first bend 162 along needle axis may improve release of the suture 20. This is shown in FIG. 12. Stated in another way, the inner member 160 may axially advance to a distal-most configuration wherein the first bend 162 is both axially and distally spaced from the needle opening proximal edge 111a. This provides a gap between the inner member 160 and proximal edge 111a of needle opening 111, allowing the suture 20 to release from the working end 104. In some embodiments, the first bend 162 is spaced axially between both a proximal edge 111a of opening 111 and a distal edge 111b of opening 111.

Figure 13:
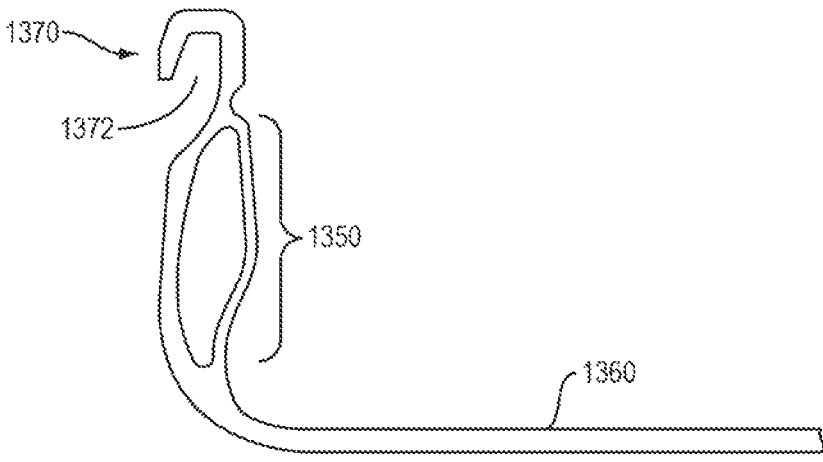
FIG. 13 illustrates another inner member hook embodiment, in accordance with this disclosure.

FIGS. 13 and 14A-14C illustrate another inner member embodiment that may have a position or setting that allows the suture to be slidingly held. This makes it easier for different types of stitches to be placed through tissue. FIG. 13 shows the inner member 1360 before assembling with needle 105 in an unstressed configuration. Inner member 1360 may be formed of a Nitinol or spring steel. Nitinol may withstand larger amounts of strain, and thereby offer larger some variations in hook trajectory as it extends in and out of the needle. Inner member distal end is configured to grab the tissue and may include a hook 1370.

Figure 14A:
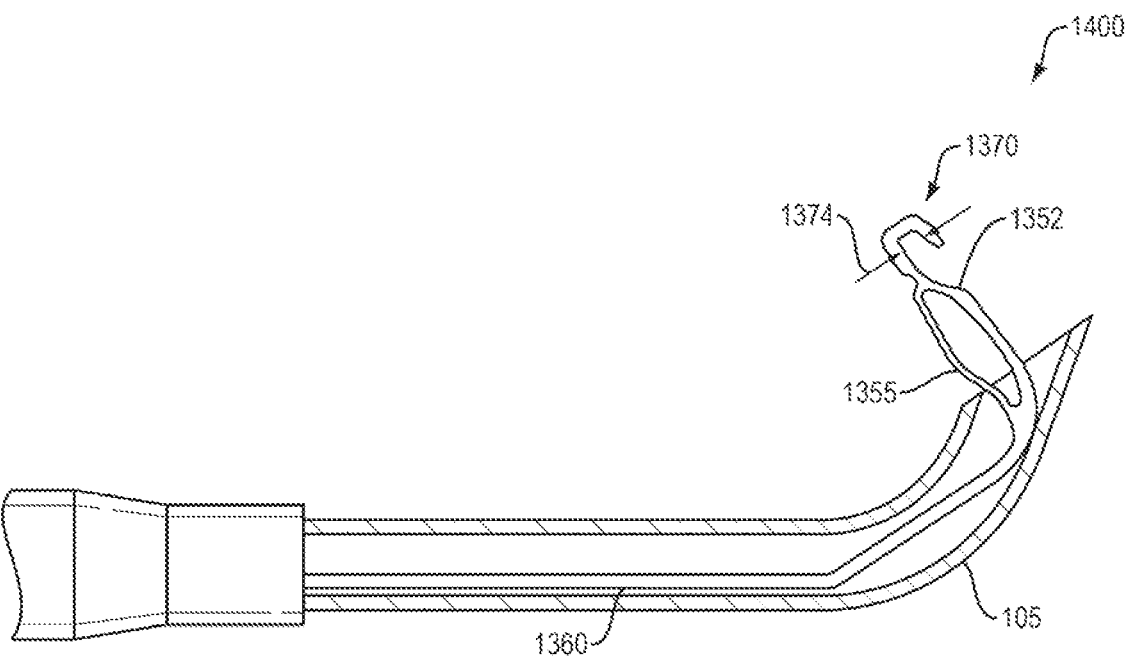
FIG. 14A illustrates a partial cross section view of needle and inner member hook, with the inner member hook in an extended configuration.
Figure 14B:
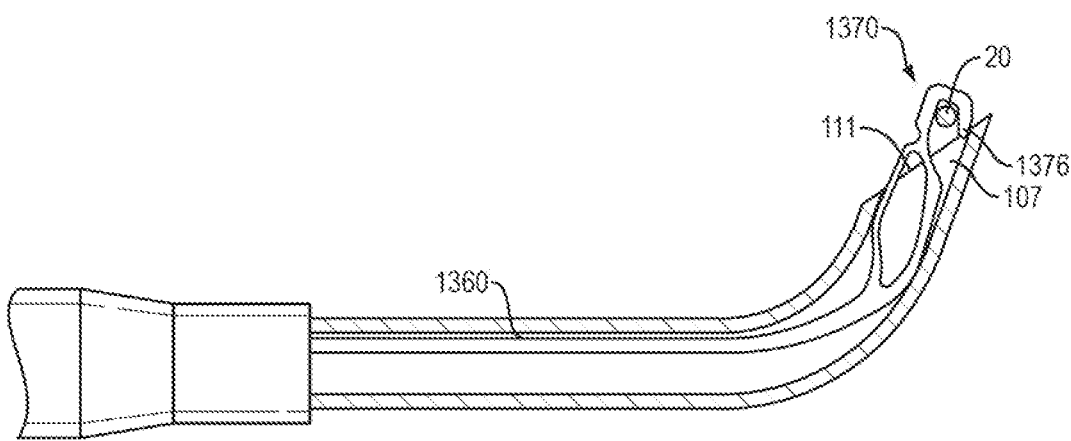
FIG. 14B illustrates a partial cross section view of needle and inner member hook, with the inner member hook in a sliding configuration.
Figure 14C:
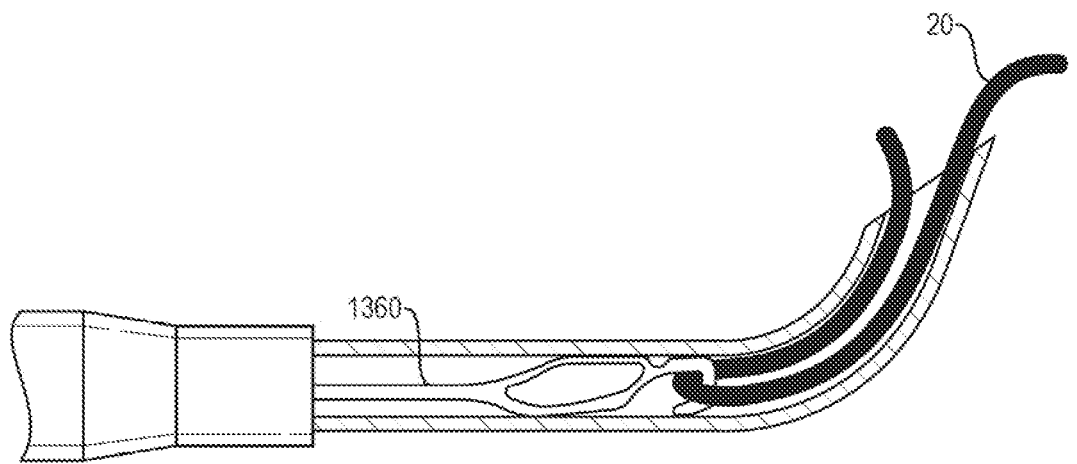
FIG. 14C illustrates a partial cross section view of needle and inner member hook, with the inner member hook in a retracted configuration.

FIG. 14A illustrates a working end 1400 of an instrument that may operate in a similar manner to instrument 100, including a needle 105, with an inner member embodiment 1360. FIG. 14A illustrates an extended configuration for engaging or releasing a suture. FIG. 14B illustrates a configuration wherein suture 20 may be held but allowed to slide through hook 1370. FIG. 14C illustrates inner member 1360 in a locking configuration.

Inner member 1360 may include a loop or bifurcated portion 1350 that defines a plurality of discrete surfaces that may be tailored to control the operation of the instrument. For example, hook 1370 defines a cavity 1372 that may be sized larger than a target suture 20 diameter. For example, for a suture diameter of 0.015, hook cavity 1372 may define a depth 1374 that is at least 0.020. This allows the suture 20 to slide through hook 1370 while in the position illustrated in FIG. 14A. As shown in the second configuration (FIG. 14B) where the suture may slide, the hook free end 1376 may be disposed within the needle lumen 107 with a distal portion of hook 1370 external to and distal to needle 105. Hook cavity 1372 is covered or enclosed by an edge surface 111. Distal facing surface 1352 of loop portion 1350 defines a curved surface configured to aim and maintain suture 20 close to the distal end of hook cavity 1372 and controls a length of suture withdrawn and ejected from the needle 105. Inner member 1360 may also include a proximally facing surface 1355 that may be curved, configured to control the trajectory of the hook 1370 as it advances and retracts. As shown proximal facing surface 1355 cooperates with a proximal most segment 111a of opening 111 to place the hook 1370 closer to the distal portion of the needle tip 108 and allow for more clearance between hook 1370 and needle 105 for suture slide. This allows the hook trajectory to be such that a slide position is achievable when the hook first engages the needle tip. Loop 1350 may define a 360 degree bounded loop. In some embodiments (not shown), loop may form a loop but include a small gap along the loop thereby defining a free end and therefore define a loop that is bounded 350 degrees for example. This gap may be preferable for manufacturing.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. An instrument for manipulating and passing a suture through a tissue, said instrument comprising:

a proximal end including a handle and a distal end including a needle, the needle defining a lumen extending up to and including a distal opening; and a hook axially moveable along the lumen between an extended configuration wherein the hook is external to the lumen configured to capture or release the suture and a retracted configuration wherein the hook is disposed within the lumen configured to hold the suture within the needle and;

wherein the hook includes three legs continuous with each other and orientated so as to define a three sided cavity to capture the suture in, the three legs including a first leg of the three legs defining a proximal-most side of the three sided cavity, extending from a first surface of the lumen and across a center axis of the lumen, a second leg of the three legs extending distally and directly from the first leg and along the center axis of the lumen and a distal-most leg extending angularly from the second leg across the center axis of the lumen defining a distal-most side of the three sided cavity, the distal-most leg having a length and angular orientation relative to a diameter of the lumen when in the retracted configuration, the distal-most leg proximally spaced from the distal opening when in the retracted configuration and wherein tension from the suture captured within the three sided cavity is configured to rotate the distal-most leg about a point (B) located along the second leg so that opposing ends of the distal-most leg interfere with at least the first surface and a second opposing surface of the lumen, to resist rotation of the distal-most leg and thereby resist release of the suture held within the hook.

2. The instrument of claim 1 wherein the hook first leg extends distally from a base portion, the base portion have a preformed bend that biases a distal-most end of the distal-most leg to engage the lumen second opposing surface when in the retracted configuration.

3. The instrument of claim 2 wherein the distal-most side of the three sided cavity is a proximal facing planar surface that extends across the center axis of the lumen, the proximal facing planar surface configured to limited cleating or recessing of the suture within the three sided cavity, and therefore easing release of suture from the three sided cavity.

4. The instrument of claim 1 wherein the hook distal-most leg defines a width that forms a lateral gap between the distal-most leg and the lumen, the lateral gap configured to bind the suture between the distal-most leg and the lumen when in the retracted configuration, and therein deter sliding of the suture through the hook.

5. The instrument of claim 4 wherein the lateral gap is 0.015 inches on each side of the hook.

6. The instrument of claim 1 wherein the needle distal lumen includes a graduated portion, including a first diameter portion that extends along the distal opening, and a second diameter portion that is smaller than the first diameter portion and extends proximally from the first diameter portion and is located at a proximal end of the distal opening, the graduated portion configured to reduce fraying of the suture, as the suture is drawn into the lumen.

7. The instrument of claim 6 wherein an outer diameter of the needle is uniform along both the first and second diameter portion.

8. The instrument of claim 6 wherein the graduated portion is also configured to reduce forces required to move the suture and hook to the retracted configuration.

9. An instrument for manipulating and passing suture through a tissue, said instrument comprising:

a handle end and a needle defining a distal end of the instrument, the needle comprising a lumen having a distal opening, the distal opening having a proximal-most edge; and a hook axially moveable within the lumen and through the distal opening;

wherein the needle lumen includes a first diameter portion that extends from the distal opening, and a second diameter portion that is smaller than the first diameter portion, and extends proximally from the proximal-most edge and first diameter portion, the first diameter portion configured to funnel the hook with a suture captured therein into the lumen with a low compression force on the suture, and the second diameter portion configured to house the suture and hook distal end within the needle, an outer diameter of the needle uniform along the first and second diameter portion.

10. The instrument of claim 9 wherein the first diameter portion transitions to the second diameter portion with a curved counterbore portion, the curved counterbore at a proximal end of the distal opening.

11. The instrument of claim 9 further comprising a tapered or rounded transition between the first and second diameter portion.

12. The instrument of claim 9 wherein the first diameter portion extends up until a proximal edge of the lumen distal opening.

13. The instrument of claim 9 wherein the second diameter portion is configured to lockingly hold the suture within the needle.

14. An instrument for manipulating and passing a suture through a tissue, said instrument comprising:

a proximal end including a handle and a distal end that defines a needle, the needle defining a lumen extending up to and including a distal opening; and a hook axially moveable along the lumen between an extended configuration wherein the hook is external to the lumen configured to capture or release the suture and a retracted configuration wherein the hook is disposed within the lumen configured to hold the suture within the needle; and wherein the hook includes three legs continuous with each other and orientated so as to define a three sided cavity to capture the suture in, the three legs including a first leg of the three legs defining a proximal-most side of the three sided cavity, extending from a first surface of the lumen and across a center axis of the lumen, a second leg of the three legs extending distally and directly from the first leg and along the center axis of the lumen and a distal-most leg extending angularly from the second leg and back across the center axis of the lumen defining a distal-most side of the three sided cavity, the distal-most side of the three sided cavity defining a planar surface that is proximally facing and extends across the center axis of the lumen, configured to engage the suture with limited cleating, and wherein the distal-most leg has a length that, when within the lumen and proximally spaced from the needle distal opening, extends from the first surface of the lumen to a second opposing surface of the lumen, at axially spaced locations along the lumen and wherein the first and second surfaces are on opposing sides of a longitudinal axis of the lumen, wherein the length is greater than a diameter of the lumen, and configured to prevent rotation of the distal-most leg via tension from the suture and thereby prevent release of the suture from the needle when in the retracted configuration.

15. The instrument of claim 14 wherein the hook distal-most leg defines a free end that is proximally spaced relative to a distal-most end of hook.

16. The instrument of claim 14 wherein the needle distal opening includes a counterbore located at a proximal end of the distal opening, configured to reduce fraying of the suture as the suture is funneled through the distal opening, past the counterbore and into the lumen.

17. The instrument of claim 16 wherein the counterbore is disposed between a first inner diameter portion that is distal to the counterbore and a second inner diameter portion that is proximal of the counterbore, the second inner diameter portion smaller than the first inner diameter portion, an outer diameter of the needle uniform along both the first and second inner diameter portions.

18. The instrument of claim 14 wherein the hook has a lateral width configured to cooperate with an inner diameter of the lumen coextensive with the hook to define a mode of a holding configuration on the suture, the mode being either a locking or a sliding hold configuration.

* * * * *